United States Patent [19]

Chauvin et al.

[11] Patent Number: 4,613,726

[45] Date of Patent: Sep. 23, 1986

[54] PROCESS FOR REMOVING NICKEL, ALUMINUM AND CHLORINE FROM OLEFIN OLIGOMERS

[75] Inventors: Yves Chauvin, Le Pecq; Dominique Commereuc, Meudon; Daniel Cruypelinck, Nanteuil le Haudoin; François Hugues, Nanterre; Georges Vidouta, Aubergenville, all of France

[73] Assignee: Institut Francais du Petrole, Rueil-Malmaison, France

[21] Appl. No.: 749,166

[22] Filed: Jun. 27, 1985

[30] Foreign Application Priority Data

Jun. 27, 1984 [FR] France ................ 84 10291

[51] Int. Cl.$^4$ ............................................ C07C 7/148
[52] U.S. Cl. .................. 585/861; 208/251 R; 208/284; 208/289; 585/531
[58] Field of Search ............ 208/251 R, 253, 284, 208/289; 585/861, 860, 531

[56] References Cited

U.S. PATENT DOCUMENTS

| | | | |
|---|---|---|---|
| 3,617,530 | 11/1971 | Rieve et al. .................... | 208/253 |
| 4,117,023 | 9/1978 | Giuet et al. .................... | 585/861 |
| 4,203,830 | 5/1980 | Rollmann et al. .............. | 208/251 R |
| 4,301,318 | 11/1981 | Beach et al. ................... | 585/531 |
| 4,320,243 | 3/1982 | Chaurin et al. ................ | 585/531 |
| 4,398,049 | 8/1983 | Le Pennec et al. ............ | 585/531 |

*Primary Examiner*—Andrew H. Metz
*Assistant Examiner*—A. Pal
*Attorney, Agent, or Firm*—Millen & White

[57] ABSTRACT

Nickel, aluminum and chlorine derivatives which remain dissolved in olefin oligomers, after oligomerization in the presence of a nickel, aluminum, and chlorine-containing catalysts, are removed by successive treatments with:

(a) anhydrous ammonia,
(b) an aqueous solution of alkali metal hydroxide, a treatment with an aqueous solution containing at least one hydroxy-acid or at least one alkali metal salt of said hydroxyacid being performed after treatment (a) and before or after or simultaneously with treatment (b), and preferably a treatment with oxygen or with an oxygen-containing gas being performed before or after treatments (a) and (b) or simultaneously with these treatments. Preferably, tartaric acid or an alkali metal tartrate is used.

20 Claims, No Drawings

PROCESS FOR REMOVING NICKEL, ALUMINUM AND CHLORINE FROM OLEFIN OLIGOMERS

The invention concerns an improved process for removing nickel, aluminum and chlorine compounds which are dissolved in raw products of monoolefins oligomerization.

BACKGROUND OF THE INVENTION

U.S. Pat. No. 3,655,810, European Pat. No. 12 685 and French Pat. No. 2 464 243, describe a process for dimerizing and/or co-dimerizing olefins, for example those having 2 to 4 carbon atoms, such as ethylene, propylene, 1 and 2-butenes, in the presence of a catalyst comprising a mixture of a nickel salt or complex, soluble in hydrocarbons, and of a hydrocarbylaluminum chloride.

In order to industrially develop this process, it is necessary to remove the inorganic part of the catalyst, the presence of which is inconvenient for many uses of the oligomers.

A mere water washing of oligomer hydrocarbons is inefficient, leading to the formation of a gelatinous alumina precipitate and resulting in the formation of chlorinated hydrocarbon derivatives and of a hydrophobic mixture of nickel hydroxide and colloidal metal nickel, which is difficult to remove from the solution. Furthermore, a substantial amount of nickel remains in the hydrocarbon phase as a soluble and stable complex, which decomposes in the reboilers during subsequent fractionations by distillation.

The use of an aqueous solution of alkali metal hydroxide avoids the formation of gelatinous alumina precipitate but does not prevent the formation of chlorinated hydrocarbons.

The treatment of the raw oligomerization product with anhydrous ammonia, followed with water washing, as described in the French Pat. No. 2 114 114, prevents the formation of chlorinated hydrocarbons but not that of a gelatinous alumina precipitate and does not eliminate the nickel compounds soluble in the hydrocarbon phase.

It has also been proposed to treat the oligomerization raw effluent, first with oxygen, then with anhydrous ammonia, and finally with an aqueous solution of alkali metal hydroxide in the presence of oxygen. This results in the destruction of the soluble nickel derivatives in the oligomers and avoids the formation of particles of hydrophobic nickel derivatives. Nickel thus precipitates as insoluble compound which apparently consists of a nickel and aluminum double hydroxide. The presence of this insoluble compound may however impede the process.

SUMMARY OF THE INVENTION

According to the invention, the liquid raw product resulting directly from the oligomerization or from the co-oligomerization of lower olefins, having 2 to 4 carbon atoms, in the presence of the above-mentioned chlorinated catalyst is (a) first treated with anhydrous ammonia and (b) finally treated with an aqueous solution of at least one hydroxide of alkali metal (Li, Na, K, Rb, Cs). The liquid raw product is treated with an aqueous solution containing at least one hydroxy-acid or at least one alkali metal salt of said acid, before or after or simultaneously with treatment (b), said treatment with a hydroxy-acid or a hydroxy-acid salt being always subsequent to treatment (a).

The hydroxy-acids or their alkali metal salts to be used are selected from the group consisting of monohydroxylated monocarboxylic acids, polyhydroxylated monocarboxylic acids, monohydroxylated polycarboxylic acids, and polyhydroxylated polycarboxylic acids.

Non limitative examples are: glycolic acid, lactic acid, salicylic acid, 3-hydroxy 2-phenyl propanoic acid, glyceric acid, 3,4-dihydroxy benzoic acid, gallic acid, tartronic acid, malic acid and tartaric acid. Preferably tartaric acid or at least one tartrate of alkali metal (Li, Na, K, Rb, Cs) are used.

The liquid raw product is preferably treated with oxygen or with an oxygen-containing gas before or after the above steps (a) and (b) or simultaneously with said steps.

By this mode of operation, all the previously described difficulties are overcome. No soluble nickel derivative remains in the hydrocarbon phase and no solid product is formed which precipitates. The total nickel and aluminum amount is dissolved in the aqueous phase, thus avoiding any eventual settling problem. The aqueous phase is separated; it can be reused in step (b); and the organic phase is recovered. Without being bound by any theory, it may be assumed that nickel and aluminum are solubilized as mixed tartarate with the alkali metal in the aqueous phase, when tartaric acid or an alkali metal tartrate is used.

This might be a disadvantage in view of the necessity of removing metals, particularly nickel, from aqueous effluents discharged from industrial plants. However, unexpectedly, the aqueous solution, after separation of the hydrocarbon phase, allows the progressive precipitation of a solid which contains the major part of the metals, and then it remains only a limpid and colorless solution which can be discharged without problems.

During the above treatment, oxygen is advantageously used in such amount that the ratio oxygen moles/nickel gram-atoms is about from 0.1:1 to 10:1 and preferably from 0.2:1 to 5:1. Oxygen may be introduced as such but it is preferable to use a mixture of oxygen with an inert gas, such for example as nitrogen or a mixture of air and nitrogen or even just air;

The oxygen proportion in the mixture is generally from 2 to 50% by volume and preferably from 3 to 30% by volume. The contact time of the oxygen-containing gas with the oligomerizate is, for example, from about 0.1 second to about 10 minutes and preferably from about 0.1 second to about 10 seconds.

For simplicity the process is described in connection with tartaric acid. However, it is equally applicable to all hydroxy-acids mentioned above and the mentioned proportions are in hydroxy-acid equivalent.

In the above treatment, the aqueous phase containing tartaric acid or at least one alkali metal tartrate contains, for example, from about 0.1 to about 20% by weight and preferably from about 0.1 to about 10% by weight of tartaric acid equivalent.

More preferably, sodium tartrate or potassium tartrate are used. The amount of tartaric acid or tartrate is such that the ratio of tartaric acid equivalent moles to the sum of aluminum and nickel gram-atoms advantageously ranges from about 0.25:1 to about 5:1, and preferably from about 0.5:1 to about 2:1.

The contact time between the organic phase and the tartaric or alkali metal tartrate aqueous solution is, for example, from about 0.1 second to about 20 minutes and preferably from about 1 second to about 5 minutes.

During the above treatment, anhydrous ammonia is added as liquid or gas. The ammonia amount is advantageously such that the ratio ammonia moles/chlorine gram-atoms present in the hydrocarbon phase, in any form, be from about 1:1 to about 10:1, preferably from about 1:1 to about 3:1. The contact time of ammonia with the hydrocarbon mixture is advantageously of the order of 0.1 second to 10 minutes, preferably from 0.1 to 10 seconds.

During the above treatment, the aqueous solution of at least one alkali metal hydroxide advantageously contains about 1 to about 25% by weight of hydroxide, preferably from about 2 to about 10% by weight. The volume ratio of the organic phase to the aqueous phase is advantageously from about 100:1 to about 1:1 and preferably from about 40:1 to about 1:1.

The contact time between the organic phase and the alkaline aqueous phase is for example from about 0.1 second to about 20 minutes, preferably from about 1 second to about 5 minutes.

A preferred embodiment of the invention consists of performing simultaneously the treatment with a tartrate aqueous solution, as above defined, simultaneously with the treatment with an alkali metal hydroxide solution. An aqueous solution of alkali metal hydroxide having 1-25% by weight hydroxide content, preferably about 2-10% by weight, and containing at least one alkali metal tartrate in a suitable amount to comply with the above-mentioned conditions, is then advantageously used.

The contact time of the organic phase with the aqueous phase is usefully from about 0.1 second to about 20 minutes and preferably from about 0.1 second to about 5 minutes; the volume ratio of the organic phase to the aqueous phase is advantageously from about 100:1 to about 1:1, preferably from about 40:1 to about 1:1.

A preferred embodiment of the invention consists, in particular, of treating the liquid raw product directly obtained by oligomerization, first with oxygen or with an oxygen-containing gas and then, in a second step, with anhydrous ammonia.

The resultant product from these two steps is then treated with an aqueous solution of alkali metal hydroxide containing at least one alkali metal tartrate, according to the above-stated conditions.

All the preceding treatments may be performed at a temperature ranging from 0° to 100° C. or more, but it is often preferable, for practical reasons, to proceed to these treatments at a temperature close to that of the oligomerization reaction, i.e. from about 20° C. to about 80° C. and preferably from about 30° C. to about 60° C.

The pressure is so selected as to be sufficient for maintaining the reaction medium in liquid state. A pressure ranging from about 0.1 megapascal (MPa) to about 5 MPa is generally satisfactory.

At the end of the treatments, the mixture separates in several phases: a gas phase consisting mainly of inert gas (e.g. nitrogen which evolves if necessary by decreasing the pressure, a basic aqueous phase and a hydrocarbon phase. The limpid aqueous phase is separated from the organic phase and may be optionally reused in another operation. The hydrocarbon phase is then washed with water and fed to the distillation unit for separation of the products.

The non-reused aqueous phase may be allowed to settle, either in the presence or absence of air, so as to form a progressive precipitate of solid containing the major part of the metals and which may then be easily separated, for example by filtration or decantation.

The process may be conducted as for oligomerization itself, batchwise or continuously.

EXAMPLES

The following examples illustrate the invention without however limiting the scope thereof.

EXAMPLE 1

A 500 ml flask provided with a magnetic stirring bar system, free of air, is fed with 200 ml of a distilled isohexenes cut dried over molecular sieve, and then with 0.85 g of nickel octoate of 10% by weight nickel content. After saturation of the liquid phase with propylene, 4.4 ml of a dichloroethylaluminum solution in hexane (50% by weight) are added, which corresponds to 14.5 mmoles of aluminum and to a molar ratio Al/Ni=10. Propylene is absorbed by said catalytic solution under a pressure of 0.13 MPa at 40° C. for 1 hour and 30 minutes. After that time, the inorganic compounds contained in the dark brown solution are removed.

By means of a syringe, 7 times 100 ml of air are introduced in said solution, this corresponding to a molar ratio $O_2/Ni=4$, while maintaining the pressure at 0.13 MPa. With the same syringe, 9 times 100 ml of ammonia gas are introduced, which corresponds to a $NH_3/Cl$ atom ratio of 1.30.

After about 10 seconds of stirring at 40° C., 43 ml of a 4% by weight sodium hydroxide aqueous solution, containing 2.65 g of tartaric acid as sodium tartrate, are injected. This corresponds to a molar ratio "tartaric acid/gram-atoms of (Al+Ni)" of 1.10.

After 4 minutes of stirring at 40° C., the hydrocarbon phase is completely discolored whereas the aqueous solution is of light green colour. The separation of the two phases takes place in a few seconds when discontinuing the stirring. No trace of suspended solids is observed. After separation, the hydrocarbon phase is essentially free of any inorganic element and contains less than 1 ppm by weight of each of nickel, aluminum and chlorine elements.

The separated aqueous phase is set in air for two days. Then it becomes completely colorless and limpid, while a green precipitate is deposited on the vessel bottom. The nickel and aluminum content of the aqueous phase, after filtration, is lower than 10 ppm by weight.

EXAMPLE 2

In the same apparatus as described in example 1, the same amount of isohexenes and catalyst are introduced.

Then, a $C_4$ cut containing 80% by weight of butenes is introduced as gas phase under a pressure of 0.1028 MPa, at a temperature of 15° C. After 2 hours of absorption, the catalyst is destroyed, according to the process described in example 1, by using the same amount of the same reactants, introduced in the same manner. The hydrocarbon phase becomes completely colorless and contains less than 1 ppm by weight of each of nickel, aluminum and chlorine elements.

The aqueous phase is of light green color and no solid suspension is observed.

What is claimed as the invention is:

1. In a process for removing aluminum, nickel and chlorine compounds from a liquid hydrocarbon reaction product obtained by oligomerization and/or co-oligomerization in liquid phase of monolefins having 2 to 4 carbon atoms, in the presence of a catalyst obtained by interaction of a nickel compound soluble in hydrocarbons with an organo-aluminum chloride, comprising the steps:

(a) treating the product with anhydrous ammonia, (b) treating the resultant product of step (a) with an aqueous solution of at least one alkali metal hydroxide, and (c) separating the aqueous phase, and recovering the organic phase, the improvement comprising treating the product of step (a) with at least one aqueous solution of at least one hydroxy-acid or at least one alkali metal salt of said hydroxy-acid, said treatment being performed before step (b), after step (b) or simultaneously with said step.

2. A process according to claim 1, further comprising treating said liquid hydrocarbon reaction product with oxygen or an oxygen-containing gas, said treatment being performed before or after steps (a) and (b) or simultaneously with said steps.

3. A process according to claim 2, wherein the oxygen content of the oxgen-containing gas is from 2 to 50% by volume.

4. A process according to claim 2, wherein the ratio "oxygen moles/nickel gram-atoms" is about 0.1:1 to about 10:1.

5. A process according to claim 1, wherein the aqueous solution used in step (b) contains about 1 to about 25% by weight of alkali metal hydroxide.

6. A process according to claim 1, wherein the aqueous solution containing at least one hydroxy-acid or at least one alkali metal salt of said hydroxy-acid contains from about 0.1 to about 20% by weight of hydroxy-acid equivalent.

7. A process according to claim 1 wherein during the one or more treatments with the aqueous solutions, in the presence of water, the ratio by volume of hydrocarbon product to aqueous solution is from about 100:1 to about 1:1.

8. A process according to claim 1, wherein the ratio of the number of hydroxy-acid equivalent moles to the sum of aluminum and nickel gram-atoms, is about 0.25:1 to about 5:1.

9. A process according to claim 1, wherein the anhydrous ammonia in step (a) is a gas or liquid and is used in a proportion of ammonia moles/chlorine gram-atoms from 1:1 to 10:1.

10. A process according to claim 1, wherein the hydroxy-acid or alkali metal salt of said hydroxy-acid is tartaric acid or an alkali metal tartrate.

11. A process according to claim 1, wherein the treatments are performed at a temperature from about 20° to about 80° C. and under a pressure from about 0.1 to about 5 MPa.

12. A process according to claim 1, wherein the hydroxy-acid or alkali metal salt of said hydroxy-acid is a monohydroxylated monocarboxylic acid, a polyhydroxylated monocarboxylic acid, a monohydroxylated polycarboxylic acid or a polyhydroxylated polycarboxylic acid.

13. A process according to claim 12, wherein the hydroxy-acid or alkali metal salt of said hydroxy-acid is glycolic acid, lactic acid, salicyclic acid, 3-hydroxy 2-phenyl propanoic acid, glyeric acid, 3,4-dihydroxy benzoic acid, gallic acid, tartronic acid, malic acid, tartaric acid, or an alkali metal salt thereof.

14. A process according to claim 1, wherein the aqueous phase separated in step (c) is recycled to step (b).

15. A process according to claim 2, wherein the oxygen-containing gas is air or a mixture of nitrogen and air.

16. A process according to claim 2, wherein the oxygen-containing gas is contacted with the liquid reaction product for about 0.1 second to about 10 minutes.

17. A process according to claim 1, wherein the hydroxy-acid or alkali metal salt thereof is contacted with the product of step (a) for about 0.1 second to about 20 minutes.

18. A process according to claim 10, wherein the product of step (a) is treated with an aqueous solution of an alkali metal tartrate simultaneously with the treatment with an aqueous solution of an alkali metal hydroxide in step (b).

19. A process according to claim 10, wherein the alkali metal salt of said hydroxy-acid is sodium tartrate.

20. A process according to claim 1, wherein the liquid reaction product is obtained by oligomerization or co-oligomerization is first treated with oxygen or an oxygen-containing gas and subsequently treated with anhydrous ammonia.

* * * * *